United States Patent
Kim et al.

(10) Patent No.: US 10,973,952 B2
(45) Date of Patent: Apr. 13, 2021

(54) MATRIX FOR RESTORING SOFT TISSUE AND PRODUCING METHOD THEREFOR

(71) Applicant: SEWONCELLONTECH CO., LTD., Seoul (KR)

(72) Inventors: Ki Soo Kim, Seoul (KR); Ji Chui Yoo, Namyangju-si (KR); Se Ken Yeo, Suwon-si (KR); Sang Bum Choi, Seoul (KR); Chang Kwon Ko, Seoul (KR); Dong Sam Suh, Seoul (KR); Cheong Ho Chang, Seoul (KR)

(73) Assignee: SEWONCELLONTECH CO., LTD., Seoul (KR)

( * ) Notice: Subject to any disclaimer, the term of this patent is extended or adjusted under 35 U.S.C. 154(b) by 819 days.

(21) Appl. No.: 15/513,049

(22) PCT Filed: Sep. 29, 2014

(86) PCT No.: PCT/KR2014/009078
§ 371 (c)(1),
(2) Date: Mar. 21, 2017

(87) PCT Pub. No.: WO2016/047834
PCT Pub. Date: Mar. 31, 2016

(65) Prior Publication Data
US 2017/0304491 A1   Oct. 26, 2017

(30) Foreign Application Priority Data
Sep. 26, 2014   (KR) .......................... 10-2014-0128919

(51) Int. Cl.
*A61L 27/24* (2006.01)
*A61L 27/26* (2006.01)

(52) U.S. Cl.
CPC .............. *A61L 27/24* (2013.01); *A61L 27/26* (2013.01); *A61L 2430/10* (2013.01); *A61L 2430/34* (2013.01)

(58) Field of Classification Search
None
See application file for complete search history.

(56) References Cited

U.S. PATENT DOCUMENTS

| | | | | |
|---|---|---|---|---|
| 4,614,794 A | * | 9/1986 | Easton | C08B 37/0084 530/356 |
| 5,916,790 A | * | 6/1999 | Enevold | B82Y 5/00 435/178 |
| 2005/0232979 A1 | * | 10/2005 | Shoshan | A61L 15/325 424/445 |
| 2006/0257377 A1 | * | 11/2006 | Atala | A61K 38/18 424/93.7 |
| 2009/0142396 A1 | * | 6/2009 | Odar | A61L 31/044 424/484 |

FOREIGN PATENT DOCUMENTS

| | | |
|---|---|---|
| KR | 10-2010-0091994 A | 8/2010 |
| KR | 10-1027630 B1 | 4/2011 |
| KR | 10-1053792 B1 | 7/2011 |
| KR | 10-1068967 B1 | 9/2011 |
| KR | 10-2012-0092494 A | 8/2012 |

* cited by examiner

*Primary Examiner* — Blaine Lankford
(74) *Attorney, Agent, or Firm* — Novick, Kim & Lee, PLLC; Jae Youn Kim (57) ABSTRACT

Disclosed are a matrix for restoring soft tissue and a method of producing the same, the method including: forming a sheet-type absorption layer (11) on one side of a double layer using biocompatible neutral collagen; forming a film-type support layer (12) on the remaining surface of the double layer by mixing collagen with a water-soluble polymer and a natural material; and forming a double layer-structured matrix (10) for restoring soft tissue by attaching the absorption layer (11) and the support layer (12) so as to treat damage to soft tissue of a mammal other than a human or restore damaged soft tissue. This invention pertains to the treatment of damage to soft tissue such as tendons, ligaments, and rotator cuffs or the restoration of damaged soft tissue, whereby the quality and reliability of products can be remarkably improved, thus satisfying various needs of consumers, who are the users thereof, and exhibiting a good effect.

13 Claims, 6 Drawing Sheets

| Classification | Gamma irradiation dose | | |
|---|---|---|---|
| Mixing ratio | 10 kGy | 25 kGy | 40 kGy |
| Collagen 0.3% + Water-soluble polymer 2.1% |  |  |  |
| Collagen 0.5% + Water-soluble polymer 1.5% |  |  |  |
| Collagen 0.7% + Water-soluble polymer 0.9% |  |  |  |

|  | 2% Neutral collagen | | 4% Neutral collagen | |
| --- | --- | --- | --- | --- |
|  | Sheet | Tensile strength | Sheet | Tensile strength |
| Collagen 0.3% + Water-soluble polymer 2.1% |  | 4.01 |  | 4.33 |
| Collagen 0.5% + Water-soluble polymer 1.5% |  | 3.44 |  | 4.26 |
| Collagen 0.7% + Water-soluble polymer 0.9% |  | 3.92 |  | 3.93 |

FIG. 6

| Mixing ratio | | | | | |
| --- | --- | --- | --- | --- | --- |
| Collagen 0.3% : Water-soluble polymer 2.1% | | Collagen 0.5% · Water-soluble polymer 1.5% | | Collagen 0.7% : Water-soluble polymer 0.9% | |
| Sheet | Tensile strength | Sheet | Tensile strength | Sheet | Tensile strength |
|  | 3.92 |  | 3.44 |  | 4.01 |

FIG. 7

MATRIX FOR RESTORING SOFT TISSUE AND PRODUCING METHOD THEREFOR

TECHNICAL FIELD

The present invention relates to a biocompatible double-layer matrix for restoring soft tissue and a method of producing the same, and more particularly to the treatment of damage to soft tissue such as tendons, ligaments and rotator cuffs, or to the restoration of damaged soft tissue, whereby the quality and reliability of products may be remarkably improved, thus satisfying a variety of needs of consumers, who are the users thereof, and exhibiting a good effect.

BACKGROUND ART

As is well known in the art, tendons, ligaments and rotator cuffs, corresponding to soft tissue, are durable fibers that connect muscles to bones or bones to bones, but may be torn, disconnected, or detached from the bones for various reasons. Such damage to soft tissue may typically result from direct external injury to relaxed soft tissue, weakening of soft tissue due to aging, eccentric loading, repetitive motion, excessive exercise and/or increased stress or activity. Such acute damage may cause long-term pain and may interfere with free exercise.

Anatomically corresponding to soft tissue, rotator cuff muscles of the shoulder joint, cruciate ligaments, lateral ligaments and patellar tendons of the knee joint, Achilles tendons, medial and lateral ligaments of the ankle joint, extensor tendons or flexor tendons of phalanges in the hand, quadriceps femoris, hamstring, etc., are common tendon and ligament injury sites in our body.

Also, with regard to damage to soft tissue such as tendons, ligaments and rotator cuffs, degenerative changes in tendons and ligaments occur with an increase in age, and thus may cause tendon tearing or ligament tearing even in the event of a minor impact or even without external injury, and are very common in older people.

According to recent studies, rotator cuff tearing drastically increases after 50 years of age, and it has been typically reported that partial-thickness tearing progresses or worsens to full-thickness tearing, and 50% of patients with partial-thickness tearing progress to full-thickness tearing, and rotator cuff tearing is observed in 50% of those in their 60s and in 80% of those in their 80s.

Furthermore, tendons, ligaments and rotator cuffs generally heal at slow rates compared to other kinds of soft tissue because of poor blood supply and a lack of cells available for tissue regeneration at the time of injury. Also, the site where the tendon is attached to the bone undergoes complicated transitional processes pertaining to the tendon, non-calcified fibrocartilage and calcified fibrocartilage because anatomical tissue portions having different physical properties are connected to each other.

Thus, tendons, ligaments and rotator cuffs exhibit quite complex and various histological and biomechanical features compared to other kinds of tissue, and also show a very different pattern from damage to tendon alone after injury of the tendon-bone junction or treatment after such damage to tendon alone, making it difficult to predict the outcome of the treatment and requiring a long period of time for treatment.

The most common sites of tendon tearing, tendon disconnection, and bone dislocation are the quadriceps (a group of four muscles: vastus lateralis, vastus medialis, vastus intermedius, and rectus femoris, which form a patellar tendon together right above the knee bone (patella)), the Achilles tendon (it is located in the back (rear) of the foot just above the heel, and functions to attach the calf muscles to the heel (calcaneus) of the feet), the rotator cuff (it is located on the shoulder and consists of four muscles (the supraspinatus (which is the most commonly torn tendon), infraspinatus, teres minor, and subscapularis), the biceps of the arm (which functions as an elbow flexor, tearing of the biceps being classified into proximal (near) tearing and distal (distant) tearing), and the flexor tendons of the hand (for example, the flexor digitorum profundus and flexor digitorum longus). The most common sites of ligament tearing, ligament disconnection, or bone dislocation are the anterior cruciate ligament (ACL), posterior cruciate ligament (PCL), and medical collateral ligament (MCL). For almost all tendon and ligament injuries, there may be significant pain (acute or chronic), limitation of movement and weakness of affected joints and limbs. For torn or detached tendons/ligaments, surgery is the most common treatment procedure to fix the tendons or ligaments to bones or to reconnect the torn or disconnected ends of affected tendons/ligaments.

For other tendon/ligament injuries, typical treatment includes resting, ice, NSAID, corticosteroid injections, heat, and ultrasound. Despite decades of research and increased clinical interest in these injuries, however, clinical outcomes thereof are still unpredictable.

With regard to the Achilles tendon, both athletes and non-athletes are at risk of injury at all ages, and most injuries occur in males aged 30 to 50 ([Boyden, E., et al., Clin Orthop, 317: 150-158 (1995)]; [Hattrup, S. and Johnson, K, Foot and Ankle, 6: 34-38 (1985)]; [Jozsa, L., et al., Acta Orthop Scandinavica, 60: 469-471 (1989)]). Achilles tendinitis and tendinosis are also common in individuals who are stressed on their ankles and feet and in "weekend warriors" who are less tempered and active on weekends only or rarely physically active.

In the case of rotator cuff injuries, despite advances in surgical instruments and techniques, current techniques are insufficient to produce enduring recovery, and in some studies, the failure rate is as high as 94%. Failure of tendon restoration may result in poor healing of the damaged tendon and poor reattachment of the damaged tendon to the bone.

Strong attachment of ligaments to the bones is also essential for many ligament reconstruction procedures. Successful ligament replacement procedures, such as anterior cruciate ligament reconstruction, require fixation of a tendon graft into the bone tunnel and progressive ingrowth of the bone into the tendon in order to produce biological attachment between the bone and the tendon. In histological and biomechanical studies, to achieve ingrowth of the bone, tendon-bone attachment, mineralization, and greater collagen-fiber continuity between the tendon and the bone, 6 to 12 weeks are required after typical insertion of a tendon graft into the bone ([Rodeo S. A. et al., Tendon-Healing in a Bone Tunnel, 75(12): 1795-1803 (1993)]).

Thus, in order to improve the healing response associated with surgical restoration or other non-surgical treatment, a novel composition and method for the treatment of various tendon/ligament injuries should be provided.

The problem pointed out in currently available operations for the restoration and regeneration of soft tissue is scarcity of graft material. These days, mainly useful treatment for restoring soft tissue includes methods using an autograft and an allograft, and materials necessary for such a grafting surgery include tendons and ligaments of humans or animals, and thus limitations are imposed on the supply thereof.

Furthermore, in the case of an autograft, pain at the sampled portion is severe and the recovery time is long.

Also, an allograft has fatal disadvantages such as weakness of transplanted organs due to sterilization, immune rejection, and the possibility of infection, for example, hepatitis or AIDS.

With the goal of solving these problems, many attempts are made to transplant biocompatible materials that help in the regeneration of soft tissue as surgical therapy of damaged soft tissue.

A biocompatible material is a substance that does not trigger rejection even when transplanted into a human body, and attempts have been made to replace damaged tissues and organs with normal tissues or to regenerate them using biocompatible materials, and thus a biocompatible material that may be transplanted into the body is receiving attention. The human body shows rejection when a foreign material is transplanted therein. Hence, it is very difficult to transplant a foreign material into the damaged site, and the development of biocompatible materials without rejection in the body has made a great contribution to the advancement of surgical medicine.

Currently, grafting medical devices to be inserted into the body are manufactured using artificial materials and natural materials.

Artificial materials, which have no vitality themselves, are composed of metals, inorganic compounds, ceramics, synthetic polymers, etc. that do not show rejection when inserted into the body and coming into contact with the surrounding tissue.

As natural materials, collagen, hyaluronic acid, chitosan, fibrin, etc. have been developed and commercialized.

Mainly useful among natural materials, collagen is a structural protein component, and forms soft tissue such as the dermis, tendons/ligaments, blood vessels and the like, and hard tissue such as bone, cartilage, etc., and constitutes about ⅓ of all proteins in mammals.

Collagen is known to have at least 20 types, and collagen type I, which forms the skin, tendons/ligaments, bone, etc., constitutes about 90% of collagen.

Collagen is a protein made up of three strands having a molecular weight of 300,000 Daltons (each strand: about 100,000 Daltons), in which the smallest unit of amino acid (with the smallest molecular weight), namely glycine, is repeatedly (-GXY-Glycine are repeated, wherein X and Y may vary) connected. Thus, glycine constitutes ⅓ of the amino acids of collagen. Furthermore, an amino acid called hydroxyproline is specifically contained in an amount of about 10% in collagen, and is thus utilized for quantitative collagen analysis methods.

Collagen is currently employed in medicine as a hemostatic agent, in wound dressings, in artificial blood vessels, and for wrinkle improvement. In the case of hemostatic agents, a collagen powder product called Avitene, obtained through extraction from calf skin in 1974, was first developed and has been used to date.

Although the properties of collagen products may vary depending on the preparation method thereof, products made of pure collagen have weak physical properties (tensile strength) and are difficult to use for suture surgery, but are excellent in terms of safety and purity. Since collagen has tensile strength and tear strength weaker than those of other polymers, it may be mixed with other materials (GAG), biocompatible synthetic polymers (PGA/PLA), water-soluble polymers (PVA, PVP), natural materials (alginate, genipin), etc.

Such collagen has advantages of low antigenicity, high biocompatibility and bioabsorbability, cell adhesion, growth and differentiation induction, blood coagulation, hemostatic effect, and compatibility with other polymers.

However, collagen has a lack of properties to maintain physical properties and volumes, and pure collagen is expensive, which is disadvantageous.

In order to solve the drawbacks of collagen, it is mixed with a biocompatible water-soluble polymer, which is any one selected from among polyvinyl alcohol, polyvinyl pyrrolidone, and polyethylene glycol, and a natural material, which is any one selected from among alginate and genipin, thus overcoming the intrinsic weakness of collagen and developing therapeutic substances with a sufficient degradation period required for regeneration, thereby making it possible to produce a biocompatible film having an excellent effect for the restoration and regeneration of soft tissue.

In the case of the development of domestic medical devices for regenerating soft tissue having many problems and side effects (studies for replacements or complements of damaged rotator cuffs, tendons, and ligaments), research on such replacements is still in the early stages in Korea and the results thereof are unsatisfactory, unlike foreign countries, in which thorough research is being actively conducted.

For this reason, therapeutic agents for regenerating soft tissue, which are currently available, may cause many side effects, and are mainly dependent on imports and are thus expensive to insure and entail material supply limitations.

CITATION LIST (Patent Document 1) Korean Patent No. 1053792 (2011 Jul. 28) (Bio-synthetic matrix and uses thereof).

DISCLOSURE

Technical Problem

Accordingly, the present invention has been made keeping in mind the above problems encountered in the related art, and the first object of the present invention is to provide the development of a formulation having a double-layer structure for the treatment of soft tissue, which is designed to solve problems of the material limitation of conventional graft products for use in soft tissue and expensive insurance coverage due to overseas production, by means of domestic development and production, and moreover which is configured such that a collagen absorption layer, which aids the regeneration of tissue, and a support layer, which is obtained by mixing biocompatible collagen with a water-soluble polymer and enables the prevention of adhesion and the control of degradability, are attached to each other. The second object of the present invention is to provide the development of a formulation having a double-layer structure, one side of which is formed with an absorption layer using neutral collagen, whereby antibiotics and agents for the regeneration or treatment of tissue may be absorbed to thus exhibit rapid regeneration and treatment compared to transplantation operations into the body. The third object of the invention is to provide the development of a formulation having a double-layer structure, wherein biocompatible collagen and a water-soluble polymer are mixed to form a film, thus developing the surface of a support having properties different from those of the surface of neutral collagen of the absorption layer, thereby preventing the adhesion of the above formulation to other tissues or organs when transplanted into the body and the regeneration of tissues other than the target tissue and controlling the degradability thereof. The fourth object of the invention is to solve the problems with a formulation composed exclusively of collagen, which cannot be used in surgery due to the low tensile strength and suture strength thereof. The fifth object of the invention is to overcome the problem of expensive insurance coverage due to autografting, allografting or foreign-made products or the limitation of supply of materials. The sixth object of the invention is to provide the development of a formulation, in which the formulation for regenerating soft tissue is inserted into the body and then naturally degrades, thus obviating the additional removal thereof. The seventh object of the invention is to develop a formulation suitable for easier and more effective operations and to realize early treatment of partial-thickness tearing upon damage to a rotator cuff, which is a kind of soft tissue, via the efficient supply of graft material through domestic production, thus solving the problem in which partial-thickness tearing progresses to full-thickness tearing. The eighth object of the invention is to provide a biocompatible matrix for restoring and regenerating soft tissue and a method of producing the same, in which the limits (serving as only a scaffold for incubating cells that constitute tissue, rather than direct materials for tissue regeneration) of conventional materials for regenerative treatment, obtained by mixing collagen with a water-soluble polymer, among the prior patents, are alleviated, and problems with materials having a single layer structure used only as a simple skin wound dressing are solved, thus enabling direct transplantation thereof into soft tissue.

Technical Solution

In order to accomplish the above objects, the present invention provides a method of producing a matrix for restoring soft tissue, comprising: forming a sheet-type absorption layer on one side of a double layer using biocompatible neutral collagen; forming a film-type support layer on the remaining side of the double layer by mixing collagen with a water-soluble polymer and a natural material; and forming a double layer-structured matrix for restoring soft tissue by attaching the absorption layer and the support layer so as to treat damage to soft tissue of a mammal other than a human or restore damaged soft tissue.

In addition, the present invention provides a matrix for restoring soft tissue, produced by the above method.

Advantageous Effects

As described hereinbefore, the present invention can provide a matrix for restoring soft tissue, which is configured to include a double layer comprising an absorption layer using neutral collagen and a support layer that is obtained by mixing collagen with a biocompatible water-soluble polymer so as to prevent adhesion to other tissues and enable the control of degradability.

In the present invention, the matrix having a double-layer structure includes the adsorption layer using neutral collagen as a biocompatible material and the support layer composed of a mixture of biocompatible collagen and water-soluble polymer, and can thus be transplanted into defective soft tissue to restore the tissue, thus effectively inducing tissue regeneration, thereby reducing the burden related to surgery of mammals other than humans and more rapidly and effectively restoring and regenerating soft tissue.

Furthermore, the present invention is able to block soft tissue from progressing from partial-thickness tearing to full-thickness tearing via the prevention and early treatment of the partial-thickness tearing thereof.

In order to accomplish the above effects, the preferred embodiments of the present invention are described in detail below with reference to the accompanying drawings.

The preferred embodiments of the present invention for achieving such effects are described in detail below with reference to the accompanying drawings.

DESCRIPTION OF THE REFERENCE NUMERALS IN THE DRAWINGS

10: matrix for restoring soft tissue
11: absorption layer
12: support layer

BEST MODE

According to the present invention, a matrix for restoring soft tissue and a method of producing the same are provided as shown in FIGS. 1 to 5.

In the following description of the present invention, it is to be noted that a detailed description of the related known functions or constructions will be omitted when it would make the gist of the present disclosure unclear.

Furthermore, the terms used herein are set taking into consideration the functions in the present invention and may vary depending on the intention of producers or usual practices, and the definitions thereof have to be determined based on the contents disclosed in the present specification.

Figure 1:
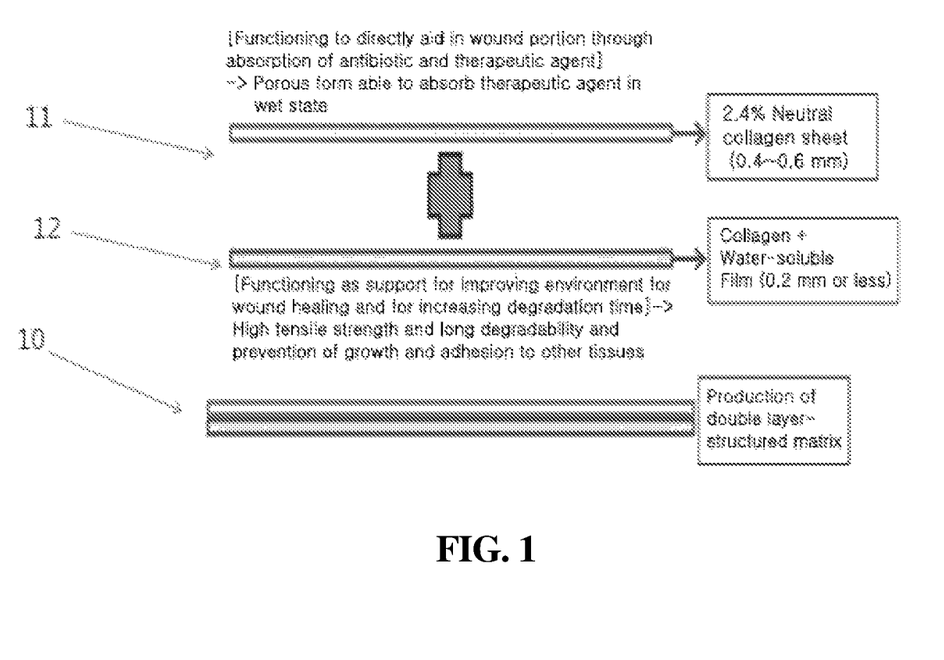
FIG. 1 shows the configuration of a matrix for restoring soft tissue according to the present invention.
Figure 2:
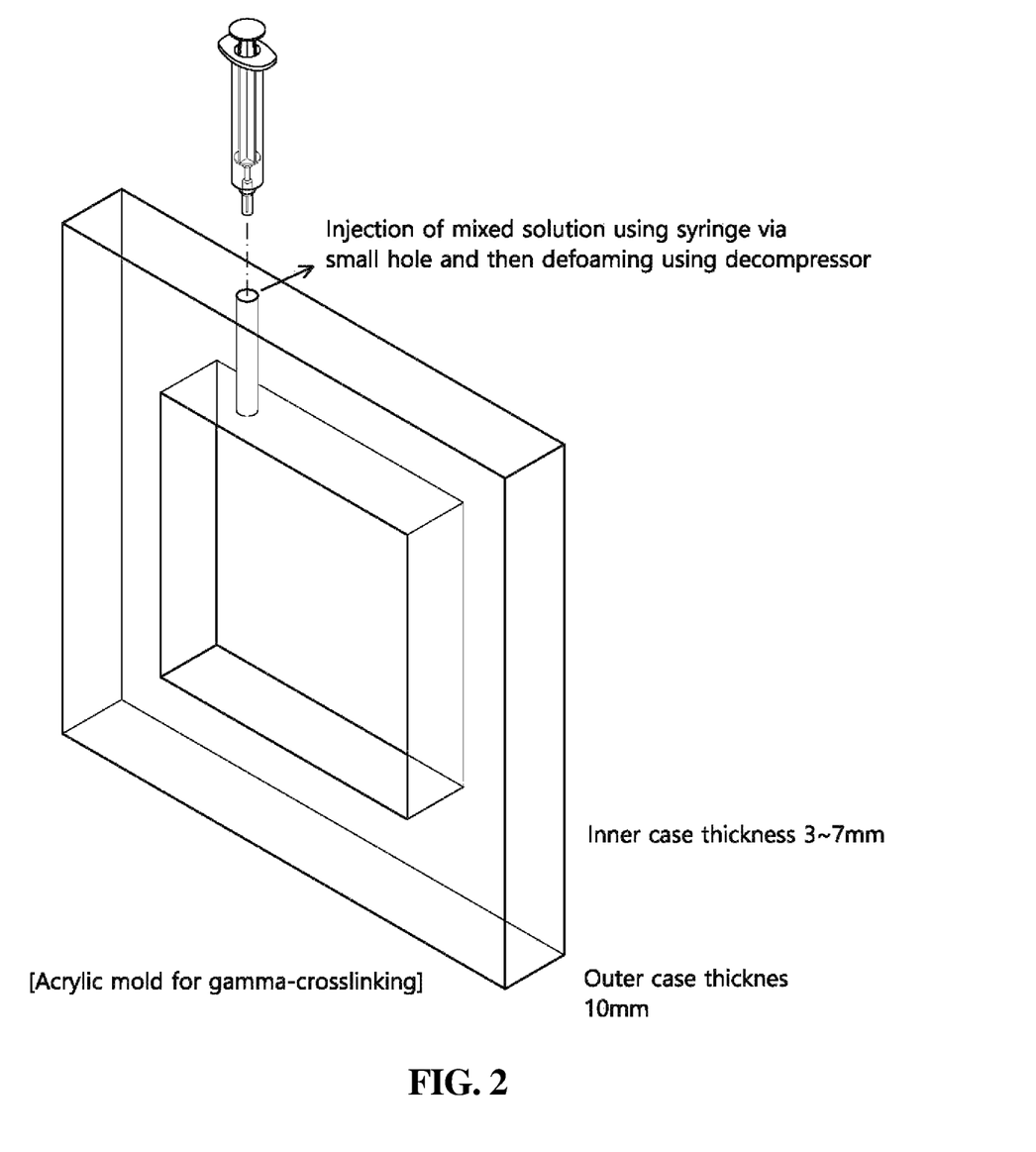
FIG. 2 shows an acrylic mold for gamma-crosslinking according to the present invention.
Figure 3:
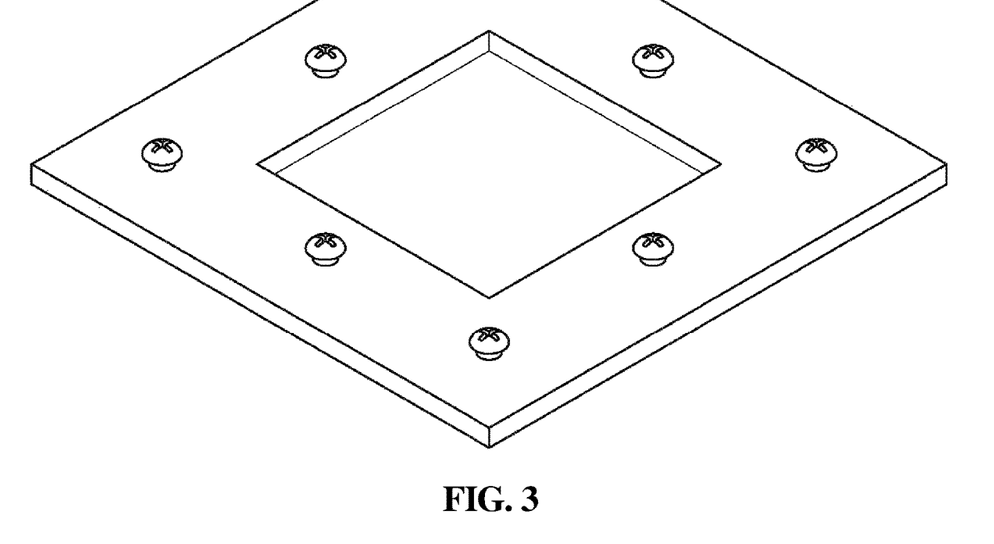
FIG. 3 shows a photograph of the acrylic mold for gamma-crosslinking according to the present invention.
Figure 4:
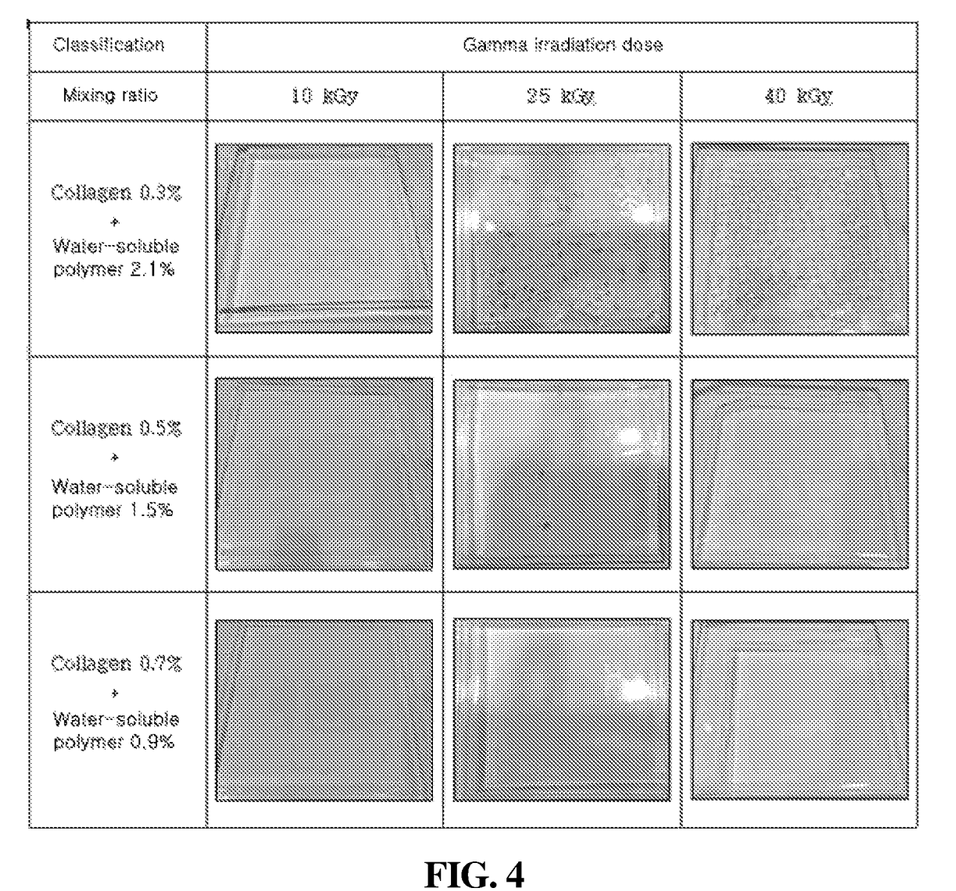
FIG. 4 shows photographs of a mixture of collagen and a water-soluble polymer, gelled after gamma-crosslinking according to the present invention.
Figure 5:
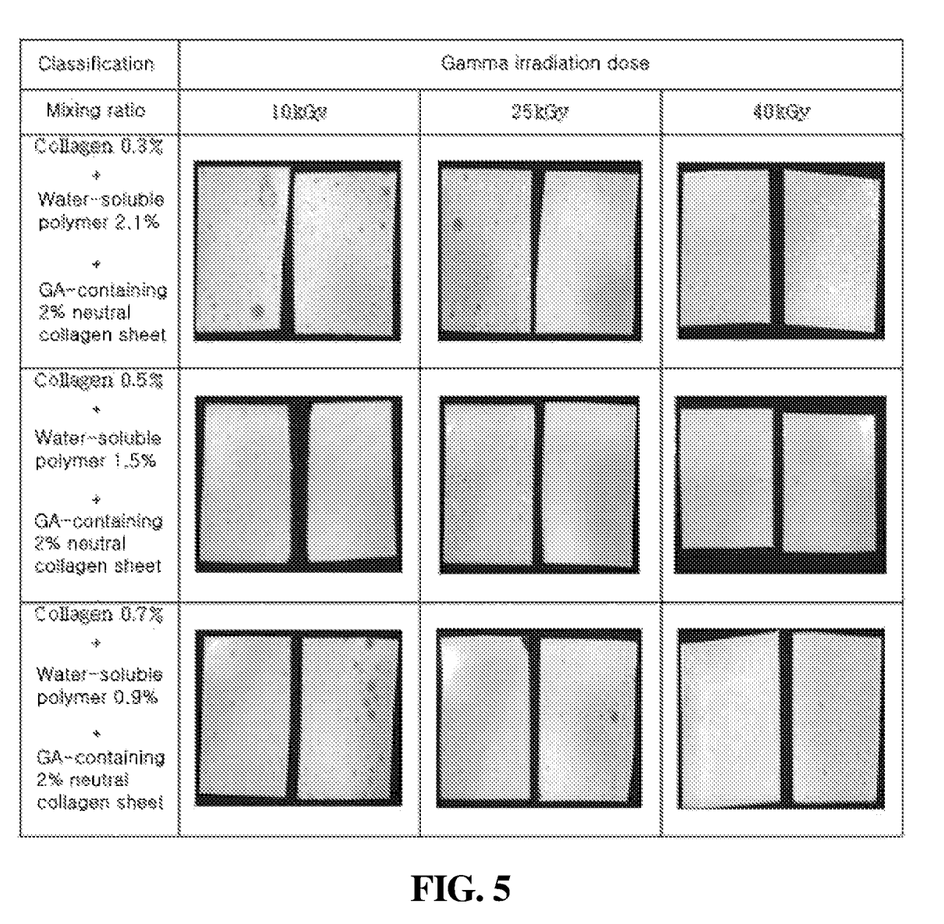
FIG. 5 shows photographs of a matrix according to the present invention, obtained by attaching an absorption layer and a support layer and then performing natural drying.

The present invention addresses a method of producing a matrix for restoring soft tissue, comprising: forming a sheet-type absorption layer 11 on one side of a double layer using biocompatible neutral collagen; forming a film-type support layer 12 on the remaining side of the double layer by mixing collagen with a water-soluble polymer and a natural material; and forming a double layer-structured matrix 10 for restoring soft tissue by attaching the absorption layer 11 and the support layer 12 so as to treat damage to soft tissue of a mammal other than a human or restore damaged soft tissue.

Here, the forming the absorption layer 11 may include: preparing neutral collagen using high-concentration collagen; gelling the neutral collagen using a crosslinking agent; forming a sheet by lyophilizing the gelled neutral collagen; subjecting the collagen in a lyophilized sheet form to DHT (dehydrothermal) treatment; and pressing the sheet form, subjected to DHT treatment, to a predetermined thickness.

In the present invention, the neutral collagen is prepared in the form of a solution having a concentration of 0.5 to 8.0% (w/w) using purified water, and is then made into a neutral collagen semi-finished product having a pH of 7.0 using NaOH.

As such, if the concentration thereof is less than 0.5%, the amount of water is excessively high compared to the amount of collagen, and thus the dry form may easily crack upon lyophilization, making it difficult to maintain the shape of a sheet. On the other hand, if the concentration thereof exceeds 8%, the viscosity is too high due to the high collagen concentration, thus causing difficulty of aliquoting for lyophilization. Hence, the above concentration preferably falls in the range of 0.5 to 8.0% (w/w) in the present invention.

In the present invention, the neutral collagen is preferably stirred using a stirrer for 80 min or more in a reaction tank at 4° C. or less.

In the present invention, the neutral collagen solution is preferably added with glutaraldehyde so that collagen is crosslinked.

As such, the amount of the crosslinking agent (glutaraldehyde) is preferably 0.4 ml (50% glutaraldehyde) or less for 1 g of collagen. If the amount of the crosslinking agent exceeds 0.4 ml (50% glutaraldehyde) for 1 g of collagen, it is greater than a biocompatible concentration. Hence, the amount thereof preferably falls in the range of 0.4 ml (50% glutaraldehyde) or less.

In the present invention, the semi-finished product containing the crosslinking agent is preferably crosslinked at a refrigeration temperature for 2 hr or more. If the stirring time is less than 2 hr, partial crosslinking of the neutral collagen solution by the crosslinking agent may occur, and crosslinking is carried out in a manner in which small lumps are present. Hence, the stirring time is preferably set to 2 hr or more.

In the present invention, 162 to 198 g of the crosslinked semi-finished product solution is preferably aliquoted in a square dish having a size of 230×230 mm, reacted at a refrigeration temperature for 24 hr or more and then gelled at room temperature for 4 hr or more and thus crosslinked. As such, only when the reaction is carried out at the above temperature for at least a predetermined period of time does crosslinking of the neutral collagen solution usable as the absorption layer occur, making it possible to manufacture a sheet.

Also, in the present invention, the subjecting the collagen in the lyophilized sheet form to DHT (dehydrothermal) treatment is performed in a manner in which the lyophilized sheet form is lyophilized in a vacuum using a dry oven at an ultralow temperature for 4 hr or more to make a sponge-type sheet, which is then pressed, thus obtaining a lyophilized sheet. If the processing time is less than 4 hr, DHT treatment does not completely occur.

Meanwhile, in the present invention, the forming the support layer 12 may include: dissolving and mixing the collagen, the water-soluble polymer, and the natural material; and crosslinking the mixed collagen.

In the present invention, the collagen is aseptically prepared in a manner in which 5 mg/mL or less of collagen is sterilized using a 0.22 μm filter and then concentrated through aseptic manipulation, and the concentration of the collagen for use in the filter is set to the range of 5 to 100 mg/mL.

In the present invention, the dissolving and mixing is performed in a manner in which, for the collagen, 0.5 to 2% (w/v) of a sterilized bio-collagen powder is mixed with a 0.1 M HCl solution having a pH of 3.0 to 4.0 and then stirred for 24 hr, and for the water-soluble polymer, 3 to 10% (w/v) of the water-soluble polymer is dissolved in water at 30° C. or more.

In the present invention, the collagen is used in an amount of 0.3 to 1.0% (w/v) and the water-soluble polymer is used in an amount of 0.9 to 2.5% (w/v).

In the present invention, the water-soluble polymer includes any one or a mixture of two or more selected from among polyvinyl alcohol, polyvinyl pyrrolidone, and polyethylene glycol.

In the present invention, the collagen and the water-soluble polymer are preferably mixed at a ratio of 1:7, 1:3, or 7:9, thus preparing a mixed solution. If the amount of collagen is less than 1:7, functionality as a therapeutic agent for restoration and regeneration do not appear. On the other hand, if the amount of the water-soluble polymer is higher than 7:9, natural degradation as a biomaterial does not occur, thus incurring degradation problems.

In the present invention, the mixed solution is placed in a mold, defoamed using a decompressor, sealed and gamma-crosslinked.

In the present invention, the crosslinking is preferably performed through physical crosslinking (UV-crosslinking, gamma-crosslinking) or chemical crosslinking (using sodium trimetaphosphate).

As such, the gamma irradiation dose is preferably set to the range of 5 to 40 kGy. If the gamma irradiation dose is less than 5 kGy, gelling of the support layer does not occur. On the other hand, if the gamma irradiation dose exceeds 40 kGy, the gel may shrink due to the high dose during the gelling of the support layer. Hence, the gamma irradiation dose preferably falls in the range of 5 to 40 kGy.

In the present invention, the natural material may be alginate.

In the present invention, the bio-collagen powder is prepared into a 1.0% (w/v) acidic collagen aqueous solution, a 3.0% (w/v) water-soluble polymer aqueous solution is prepared, and the two aqueous solutions are mixed so that the amount of collagen is 0.3 to 0.7% (w/v) and the amount of the water-soluble polymer is 0.9 to 2.5% (w/v) based on the total weight thereof to give a mixed solution, which is then gamma-crosslinked at a gamma irradiation dose of 5 to 40 kGy, thus forming a harmless film-type support layer.

Also, the present invention addresses a matrix for restoring soft tissue, manufactured by the aforementioned method.

The present invention may be variously modified upon the application of the above configuration and may be provided in diverse forms.

It is also to be understood that the present invention is not limited to the specific forms described above but is to be regarded as including all of the modifications, equivalents and substitutions within the spirit and scope of the present invention defined by the accompanying claims.

A better understanding of the matrix for restoring soft tissue and the method of producing the same according to the present invention may be obtained through the following Examples.

The present invention pertains to the treatment of damage to soft tissue such as tendons, ligaments, and rotator cuffs or to the restoration of damaged soft tissue.

Specific embodiments of the present invention are described below.

Example 1—Formation of Absorption Layer

A method of forming a sheet-type absorption layer, which is harmless and may be applied to humans by making high-concentration collagen into 0.5 to 8.0% (w/w) neutral collagen, is provided. Here, a sheet contains 2%, 4% (w/w) collagen and a crosslinking agent (glutaraldehyde) in an amount of 0.4 ml (50% glutaraldehyde) or less per g of collagen. The most appropriate thickness of the absorption layer is set to the range of 0.4 to 0.6 mm through pressing. If the amount of collagen is less than 2%, the dried sheet form may be easily broken and the shape thereof may be difficult to maintain. On the other hand, if the amount thereof exceeds 4%, the dried sheet may break down when subjected to a force due to poor flexibility after attachment to the support layer. If the amount of the crosslinking agent is greater than 0.4 ml for 1 g of collagen, an appropriate biocompatible concentration is exceeded. Hence, the amount of the crosslinking agent is set to 0.4 ml (50% glutaraldehyde) or less. Since the sheet of the present invention covers the damaged portion upon operation for restoring and regenerating soft tissue, a sheet having a thickness less than 0.4 mm (50% glutaraldehyde) may be very weak, whereas a matrix having a thickness greater than 0.6 mm is cumbersome when used in operation, which does not satisfy the purpose of the present invention.

Formation of Neutral Collagen Absorption Layer Containing 2%, 4% Collagen

1) A bio-collagen solution having a high concentration of 5% or more is prepared into a collagen solution having a concentration of 2%, 4% (w/w) using purified water, and then the pH thereof is adjusted to 7.0 using NaOH, thus manufacturing a semi-finished product. The reason why the concentration is set as above is as described above. In the case of acidity or alkalinity other than a pH of 7.0, the resulting solution may cause problems when injected into the body, and hence the neutral collagen is used for the formation of a sheet.

2) The neutral collagen semi-finished product thus formed is stirred in a reaction tank at 4° C. or less for 80 min or more. If the stirring is not performed for at least a predetermined period of time, the neutral collagen diluted to a low concentration from a high concentration is not present in the form of a uniform solution but is lumpy, which is undesirable.

3) The mixed collagen solution is mixed with a crosslinking agent such as glutaraldehyde in an amount of 0.4 ml (50% glutaraldehyde) per g of collagen, and then stirred at 4° C. or less for 2 hr or more. The crosslinking is carried out at a refrigeration temperature for 2 hr or more. If the stirring is not performed for 2 hr or more, the neutral collagen solution may be partially crosslinked by means of the crosslinking agent, thus forming small lumps.

4) The neutral collagen mixed with the crosslinking agent is aliquoted into a 230×230 mm-sized square dish in an amount of 162 to 198 g each, reacted at 4° C. for 72 hr or more, and then gelled at 25° C. for 8 hr or more. Only when the reaction is carried out at the aforementioned temperature for at least a predetermined period of time does crosslinking of the neutral collagen solution usable as the absorption layer occur, making it possible to manufacture a sheet.

5) The gelled neutral collagen semi-finished product is frozen and then lyophilized in a vacuum using a freeze dryer. In the case where the gelled semi-finished product is lyophilized in a vacuum without freezing, many cracks may form on the surface of the dried sheet.

6) The lyophilized sheet is subjected to DHT treatment at 110° C. to 140° C. for 4 hr or more using a dry oven. If this process is performed at a temperature lower than 110° C. or for a period of time less than 4 hr, DHT treatment does not completely occur. On the other hand, if this process is performed at a temperature higher than 140° C., the sheet may be burned.

7) The sheet is pressed to a predetermined thickness of 0.4 to 0.6 mm using a pressing machine. The sheet of the present invention has to possess a thickness suitable for covering the damaged portion upon operation for restoring or regenerating soft tissue. If the thickness thereof is less than 0.4 mm, strength may be too low. On the other hand, if the thickness thereof is greater than 0.6 mm, the resulting matrix is cumbersome when used in operation, which does not satisfy the purpose of the invention.

Example 2—Production of Double-Layer Matrix by Forming Support Layer and then Attaching it to Absorption Layer An aseptic bio-collagen powder is prepared into a 1.0% (w/v) acidic collagen aqueous solution, and a 3.0% (w/v) water-soluble polymer aqueous solution is prepared, and these two aqueous solutions are mixed so that the amount of collagen is 0.3 to 0.7% (w/v) and the amount of the water-soluble polymer is 0.9 to 2.5% (w/v), based on the total weight thereof, thus obtaining a mixed solution. Here, if the amount of collagen is less than 0.3%, it is too low to serve for restoring and regenerating soft tissue according to the present invention. On the other hand, if the amount thereof exceeds 0.7%, it is difficult to carry out the gelling process during the formation of the support layer. If the amount of the water-soluble polymer is less than 0.9%, it is difficult to maintain the shape of the support layer and the physical properties thereof, especially tensile strength. On the other hand, if the amount thereof exceeds 2.5%, degradability may become problematic due to the excessive amount of the water-soluble polymer. After the mixing of the collagen and the water-soluble polymer at the above mixing ratio, gamma-crosslinking is performed at a gamma irradiation dose of 5 to 40 kGy, thereby manufacturing a film-type support layer, which is harmless and is applicable to humans. Here, the gamma irradiation dose is appropriately set to the range of 5 to 40 kGy. If the gamma irradiation dose is less than 5 kGy, crosslinking is not performed due to the excessively low dose and thus gelling cannot be achieved. On the other hand, if the gamma irradiation dose exceeds 40 kGy, the gel may shrink due to the excessively high dose during the crosslinking and the resulting gel may be deformed during the drying. Hence, the gamma irradiation dose is set to the range of 5 to 40 kGy.

1) 0.5 to 2% (w/v) of an aseptic bio-collagen powder is mixed with a 0.1 M HCl solution having a pH of 3.0 to 4.0 and is stirred for 24 hr or more, and a water-soluble polymer selected from among polyvinyl alcohol, polyvinyl pyrrolidone and polyethylene glycol is dissolved in an amount of 3 to 10% (w/v) in water at 30° C. or more for 2 hr or more. In this procedure, an acidic pH less than 3.0 upon dissolution of collagen may cause a problem in terms of using a product that is injected into the body due to strong acidity, whereas a pH greater than 4.0 may be problematic in that the collagen powder is not dissolved well. Furthermore, the water-soluble polymer does not dissolve during the dissolving process at a temperature of less than 30° C.

2) The biocompatible aqueous solutions prepared above are mixed so that the amount of the collagen is 0.3 to 0.7% (w/v) and the amount of the water-soluble polymer is 0.9 to 2.5% (w/v) based on the total weight thereof, and are then stirred for 24 hr or more. If the amount of the collagen is less than 0.3%, it is too low to serve for restoring and regenerating soft tissue, which is the purpose of the present invention. On the other hand, if the amount thereof exceeds 0.7%, it is difficult to perform the gelling process during the manufacture of the support layer. Also, if the amount of the water-soluble polymer is less than 0.9%, it is difficult to maintain the shape of the support layer and physical properties such as tensile strength thereof. On the other hand, if the amount thereof exceeds 2.5%, degradability may become problematic due to the excessively large amount of the water-soluble polymer. Furthermore, if the stirring time is less than 24 hr, the solutions are not mixed well but are non-uniformly mixed.

3) The mixed semi-finished product is injected in an amount of 55 to 110 g into an acrylic mold having a size of 100×100×5 mm/120×120×7 mm and then sealed. Here, it should be noted that the size of the mold should be set to be equal to or larger than a minimum standard for tensile strength measurement and also that the mold should be fully filled with the mixed semi-finished product while preventing the generation of foam.

4) The semi-finished product is gamma-crosslinked at a gamma irradiation dose of 5 to 40 kGy so as to be gelled. If the gamma irradiation dose is less than 5 kGy, the mixed solution is not efficiently gelled. On the other hand, if the gamma irradiation dose exceeds 40 kGy, the dried form may become curved during the drying process. Hence, the gamma irradiation dose is optimally set to the range of 5 to 40 kGy.

5) The biocompatible mixture, gelled by completing the crosslinking at a gamma irradiation dose of 5 to 40 kGy, is coated with the neutral collagen absorption layer and then completely dried through natural drying for 48 hr or more, thereby producing a double-layer matrix for restoring soft tissue. Drying for less than 48 hr may result in an incompletely dried form.

In the present invention, changes in properties depending on the difference in concentration of neutral collagen of the absorption layer and comparison of properties depending on the mixing ratio of collagen and the water-soluble polymer of the support layer and on the gamma irradiation dose are as follows.

Changes in properties depending on the concentration of neutral collagen of absorption layer.

A matrix solid, obtained by attaching each absorption layer, containing different amounts of collagen, to the support layer, is measured for the properties using UTM. The conditions are described below.

Measurement item: Tensile strength, elongation
Load cell: 20 N, 200 N
Test rate: 5 mm/min
Span: 30 mm
Test temperature: (23±2)° C., (50±5)% RH
Sample width: 10 mm
Hydration conditions: Immersion of sample in DI water for 10 min
The results are as follows.

Figure 6:
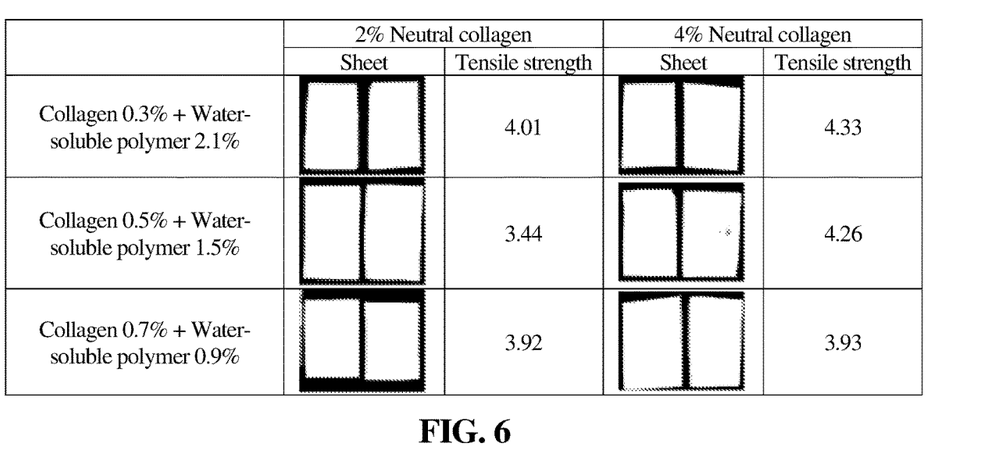
FIG. 6 shows changes in properties depending on the concentration of neutral collagen of absorption layer.

Changes in properties when attaching each of the absorption layers containing collagen in different amounts to the support layer (Gamma irradiation dose: 5 to 40 kGy) are shown in FIG. 6.

Figure 7:
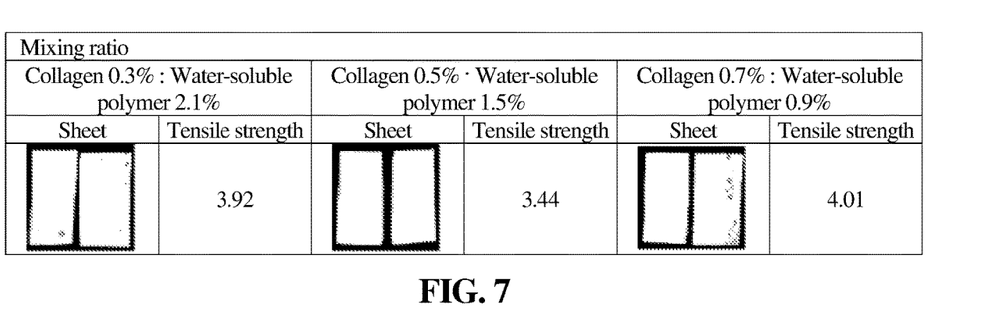
FIG. 7 shows changes in properties depending on the mixing ratio of the collagen and the water-soluble polymer of the support layer (Gamma irradiation dose: 5 to 40 kGy).

2) Changes in properties depending on the mixing ratio of the collagen and the water-soluble polymer of the support layer (Gamma irradiation dose: 5 to 40 kGy) are shown in FIG. 7.

3) Changes in properties depending on gamma irradiation dose

The absorption layer containing 2% of collagen is attached to the support layer obtained by mixing 0.3 to 0.7% (w/v) of collagen and 0.9 to 2.5% (w/v) of the water-soluble polymer and then applying different gamma irradiation doses, thus obtaining individual matrixes, the properties of which are then measured using UTM. The conditions are as follows.

Measurement item: Tensile strength, elongation
Load cell: 20 N, 200 N
Test rate: 5 mm/min
Span: 30 mm
Test temperature: (23±2)° C., (50±5)% RH
Sample width: 10 mm
Hydration conditions: Immersion of sample in DI water for 10 min
The results are described below in table 1.

TABLE 3

|  | Dose | | | | | | | | |
| --- | --- | --- | --- | --- | --- | --- | --- | --- | --- |
|  | 10 kGy | | | 25 kGy | | | 40 kGy | | |
| Mixing ratio | 0.3:2.1 | 0.5:1.5 | 0.7:0.9 | 0.3:2.1 | 0.5:1.5 | 0.7:0.9 | 0.3:2.1 | 0.5:1.5 | 0.7:0.9 |
| Tensile strength | 3.92 | 3.44 | 4.01 | 4.38 | 2.04 | 6.95 | 2.87 | 6.18 | 4.77 |

INDUSTRIAL APPLICABILITY

The technical idea of the present invention regarding the matrix for restoring soft tissue and the method of producing the same is able to obtain consistent results in practice. In particular, the present invention promotes technical development and can contribute to industrial development and is thus worth protecting.

The invention claimed is:

1. A method of producing a double layer-structured matrix for treating or restoring damaged soft tissue, the method comprising:
    forming a sheet-type absorption layer using biocompatible neutral collagen, wherein the neutral collagen has pH of 7.0, and the sheet-type absorption layer is porous;
    forming a film-type support layer by mixing collagen with a water-soluble polymer and a natural material comprising alginate; and
    forming the double layer-structured matrix by attaching the absorption layer and the support layer,
    wherein the forming of the sheet-type absorption layer comprises:
        preparing a neutral collagen solution using collagen having a concentration of 0.5 to 8.0% (w/w);
        gelling the neutral collagen solution using glutaraldehyde as a crosslinking agent;

forming a sheet by lyophilizing the gelled neutral collagen;
subjecting the formed sheet to dehydrothermal treatment; and
pressing the formed sheet subjected to the dehydrothermal treatment to a predetermined thickness,
wherein the forming of the film-type support layer comprises:
dissolving and mixing a collagen solution and the water-soluble polymer at a ratio of 1:7 to 7:9, together with the natural material comprising alginate to prepare a mixed solution; and
crosslinking the mixed solution by placing the mixed solution in a mold, defoaming the mixed solution using a decompressor, and sealing and gamma-crosslinking the defoamed mixed solution at a gamma irradiation dose of 5 to 40 kGy, and
wherein the sheet-type absorption layer has a thickness of 0.4 to 0.5 mm and the film-type support layer has a thickness of 0.2 mm or less.

2. The method of claim 1, wherein the collagen having the concentration of 0.5 to 8.0% (w/w) is prepared using purified water, and is then made into the neutral collagen solution having a pH of 7.0 using NaOH.

3. The method of claim 1, wherein the neutral collagen solution is stirred using a stirrer for 80 minutes or more in a reaction tank at 4° C. or less.

4. The method of claim 1, wherein the glutaraldehyde is used in an amount of 0.4 ml or less of 50% w/w glutaraldehyde for 1 g of collagen.

5. The method of claim 1, wherein the neutral collagen solution containing the crosslinking agent is crosslinked at a refrigeration temperature for 2 hours or more.

6. The method of claim 1, wherein 162 to 198 g of the crosslinked neutral collagen solution is aliquoted in a square dish having a size of 230×230 mm, reacted at a refrigeration temperature for 24 hours or more and then gelled at room temperature for 4 hours or more and thus crosslinked.

7. The method of claim 1, wherein the subjecting the formed sheet to dehydrothermal treatment is performed in a manner in which the gelled neutral collagen is lyophilized in a vacuum using a dry oven at a temperature of −20° C. or less for 4 hours or more to make a sponge-type sheet, which is then pressed, thus obtaining a lyophilized sheet.

8. The method of claim 1, wherein the collagen is aseptically prepared in a manner in which 5 mg/mL or less of collagen is sterilized using a 0.22 μm filter and then concentrated through aseptic manipulation, and a concentration of the collagen for use in the filter ranges from 5 to 100 mg/mL.

9. The method of claim 1, wherein the dissolving and mixing is performed in a manner in which, for the collagen solution, 0.5 to 2% (w/v) of a sterilized biocompatible collagen powder is mixed with a 0.1 M HCl solution having a pH of 3.0 to 4.0 and is then stirred for 24 hours, and for the water-soluble polymer, 3 to 10% (w/v) of the water-soluble polymer is dissolved in water at 30° C. or more.

10. The method of claim 1, wherein the collagen is used in an amount of 0.3 to 1.0% (w/v) and the water-soluble polymer is used in an amount of 0.9 to 2.5% (w/v).

11. The method of claim 1, wherein the water-soluble polymer comprises one or more selected from the group consisting of polyvinyl alcohol, polyvinyl pyrrolidone, and polyethylene glycol.

12. The method of claim 1, wherein the crosslinking is performed through physical crosslinking or chemical crosslinking.

13. The method of claim 9, wherein the biocompatible collagen powder is prepared into a 1.0% (w/v) acidic collagen aqueous solution, a 3.0% (w/v) water-soluble polymer aqueous solution is prepared, and the two aqueous solutions are mixed so that an amount of the collagen is 0.3 to 0.7% (w/v) and an amount of the water-soluble polymer is 0.9 to 2.5% (w/v) based on a total weight thereof to form a mixed solution, which is then gamma-crosslinked at a gamma irradiation dose of 5 to 40 kGy, thus forming the film-type support layer.

* * * * *